US011039777B2

(12) United States Patent
Honjo et al.

(10) Patent No.: US 11,039,777 B2
(45) Date of Patent: Jun. 22, 2021

(54) ULTRASONIC DIAGNOSTIC APPARATUS AND CONTROL METHOD

(71) Applicant: Toshiba Medical Systems Corporation, Otawara (JP)

(72) Inventors: Yasunori Honjo, Nasushiobara (JP);
Tetsuya Kawagishi, Nasushiobara (JP);
Akihiro Kakee, Nasushiobara (JP);
Yuko Kanayama, Nasushiobara (JP);
Masaki Watanabe, Takanezawa (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1028 days.

(21) Appl. No.: 15/184,328

(22) Filed: Jun. 16, 2016

(65) Prior Publication Data
US 2016/0367223 A1   Dec. 22, 2016

(30) Foreign Application Priority Data
Jun. 17, 2015   (JP) .............................. JP2015-122353

(51) Int. Cl.
*A61B 8/00* (2006.01)
*A61B 8/08* (2006.01)
(Continued)

(52) U.S. Cl.
CPC ............ *A61B 5/318* (2021.01); *A61B 5/7285* (2013.01); *A61B 8/485* (2013.01); *A61B 8/488* (2013.01);
(Continued)

(58) Field of Classification Search
CPC .. A61B 8/00; A61B 8/08; A61B 8/485; A61B 8/54; A61B 8/543; A61B 8/5215;
(Continued)

(56) References Cited

U.S. PATENT DOCUMENTS

| 2015/0119710 A1* | 4/2015 | Kawae | A61B 8/485 600/438 |
| 2015/0119712 A1* | 4/2015 | Tanigawa | A61B 8/485 600/438 |
| 2017/0035384 A1* | 2/2017 | Sonoyama | A61B 8/08 |

FOREIGN PATENT DOCUMENTS

| JP | 2001-292995 A | 10/2001 |
| JP | 2014-260 | 1/2014 |

(Continued)

OTHER PUBLICATIONS

Office Action dated Sep. 3, 2019 in Japanese Patent Application No. 2015-122353.
(Continued)

*Primary Examiner* — Carolyn A Pehlke
(74) *Attorney, Agent, or Firm* — Oblon, McClelland, Maier & Neustadt, L.L.P.

(57) ABSTRACT

An ultrasonic diagnostic apparatus according to an embodiment includes calculation circuitry, acquisition circuitry, determination circuitry, and scan control circuitry. The calculation circuitry calculates an indicator related to motion of biological tissue in a subject, based on echo data obtained through a pre-scan for the subject. The acquisition circuitry acquires a periodic biological signal of the subject. The determination circuitry specifies at least one tune phase in one cycle of the biological signal acquired during the pre-scan, based on the indicator, and determines a timing of a main scan for the subject, based on the specified time phase and the biological signal acquired after the pre-scan. The scan control circuitry executes the main scan at the timing determined by the determination circuitry.

14 Claims, 10 Drawing Sheets

(51) Int. Cl.
*A61B 8/14* (2006.01)
*A61B 5/318* (2021.01)
*G01S 7/52* (2006.01)
*A61B 5/00* (2006.01)

(52) U.S. Cl.
CPC .............. *A61B 8/5246* (2013.01); *A61B 8/54* (2013.01); *A61B 8/543* (2013.01); *G01S 7/52042* (2013.01); *G01S 7/52088* (2013.01); *A61B 8/14* (2013.01); *A61B 8/461* (2013.01); *A61B 8/467* (2013.01)

(58) Field of Classification Search
CPC ........... A61B 8/14; A61B 8/461; A61B 8/467; A61B 5/0402; A61B 5/7285; A61B 6/541; G01R 33/567
See application file for complete search history.

(56) References Cited

FOREIGN PATENT DOCUMENTS

| | | |
|---|---|---|
| JP | 2015-23913 A | 2/2015 |
| JP | 2015-29610 A | 2/2015 |
| JP | 2015-107311 A | 6/2015 |
| WO | WO 2011/034005 A1 | 3/2011 |
| WO | WO 2012/023399 A1 | 2/2012 |

OTHER PUBLICATIONS

Office Action dated Dec. 17, 2019 in corresponding Japanese Patent Application No. 2015-122353, 4 pages.
Office Action dated Mar. 19, 2019 in corresponding Japanese Patent Application No. 2015-122353.

\* cited by examiner

ULTRASONIC DIAGNOSTIC APPARATUS AND CONTROL METHOD

CROSS-REFERENCE TO RELATED APPLICATIONS

This application is based upon and claims the benefit of priority from Japanese Patent Application No. 2015-122353, filed on Jun. 17, 2015; the entire contents of which are incorporated herein by reference.

FIELD

Embodiments described herein relate generally to an ultrasonic diagnostic apparatus and a control method.

BACKGROUND

Elastography has been known, which measures the stiffness of biological tissue and visualizes the distribution of the measured stiffness. Elastography is used, for example, for diagnosis of diseases such as cirrhosis that change the stiffness of biological tissue with the degree of progress of lesions.

In elastography, the stiffness of biological tissue is evaluated, for example, by giving acoustic radiation force or mechanical vibration to biological tissue from the body surface using an ultrasound probe to produce shear wave-induced displacement, and observing the displacement at each point in the scanned section over time to obtain the propagation speed of shear waves and then the elastic modulus.

DETAILED DESCRIPTION

An ultrasonic diagnostic apparatus according to an embodiment includes calculation circuitry, acquisition circuitry, determination circuitry, and scan control circuitry. The calculation circuitry calculates an indicator related to motion of biological tissue in a subject, based on echo data obtained through a pre-scan for the subject. The acquisition circuitry acquires a periodic biological signal of the subject. The determination circuitry specifies at least one time phase in one cycle of the biological signal acquired during the pre-scan, based on the indicator, and determines a timing of a main scan for the subject, based on the specified time phase and the biological signal acquired after the pre-scan. The scan control circuitry executes the main scan at the timing determined by the determination circuitry.

Embodiments of an ultrasonic diagnostic apparatus and a control method will be described in details below with reference to the accompanying drawings. The embodiments can be combined as appropriate.

First Embodiment

Figure 1:
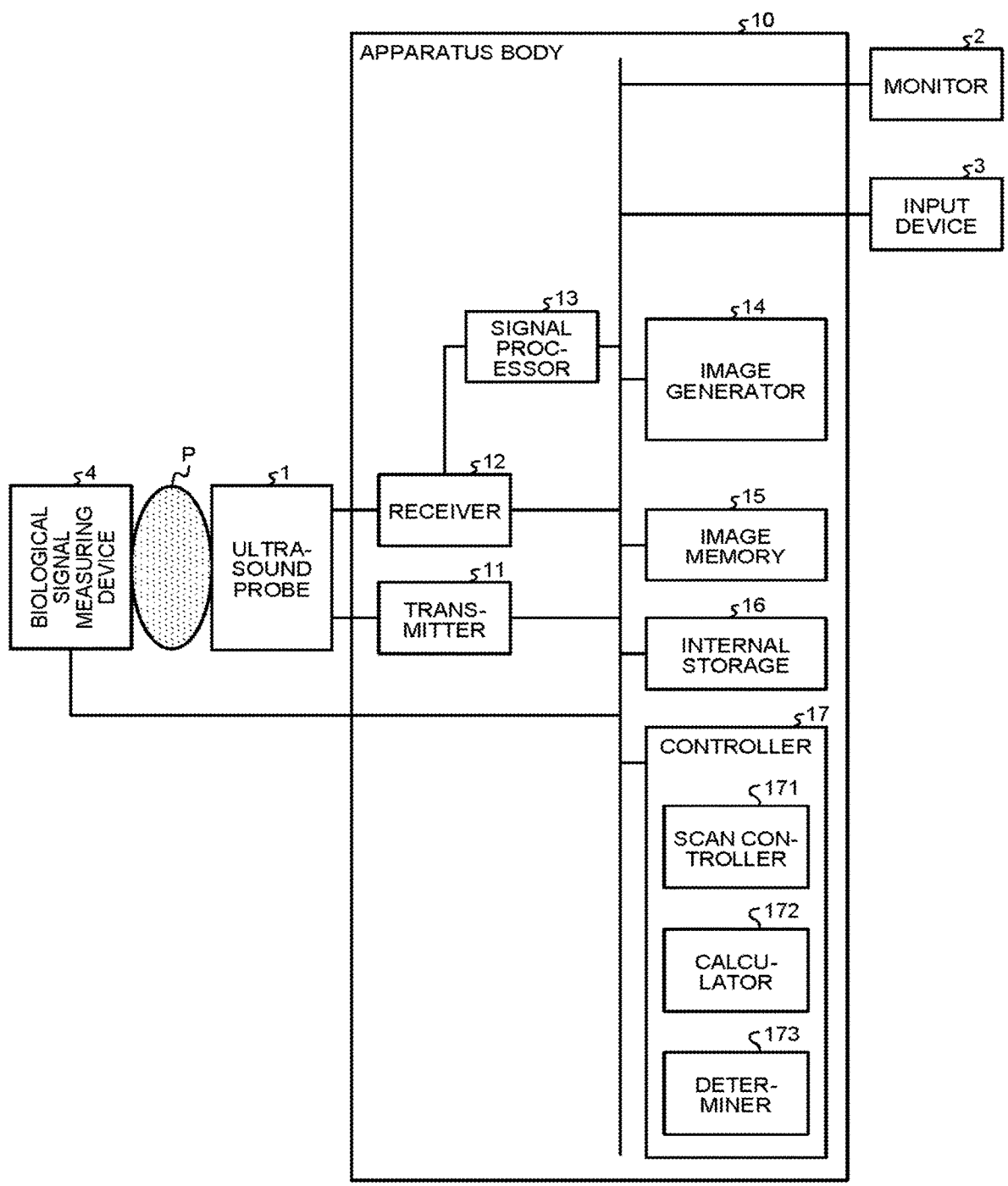
FIG. 1 is a block diagram illustrating a configuration example of an ultrasonic diagnostic apparatus according to a first embodiment.

A configuration of an ultrasonic diagnostic apparatus according to a first embodiment will now be described. FIG. 1 is a block diagram illustrating a configuration example of the ultrasonic diagnostic apparatus according to the first embodiment. As illustrated in FIG. 1, the ultrasonic diagnostic apparatus according to the first embodiment includes an ultrasound probe 1, a monitor 2, an input device 3, and an apparatus body 10. The apparatus body 10 is connected to a biological signal measuring device 4.

The ultrasound probe 1 includes a plurality of transducer elements (for example, piezo transducer elements). Theses transducer elements produce ultrasound based on a drive signal supplied from a transmitter 11 in the apparatus body 10 described later. The transducer elements of the ultrasound probe 1 convert an echo received from a subject P into an electrical signal (echo signal). The ultrasound probe 1 further includes a matching layer provided on the transducer elements and a backing material for preventing ultrasound from propagating to the back side of the transducer elements.

When ultrasound is transmitted from the ultrasound probe 1 to the subject P, the transmitted ultrasound is reflected one after another at the acoustic impedance discontinuous surface in biological tissue of the subject P and received as echoes by the transducer elements of the ultrasound probe 1. The amplitude of an echo signal produced from the received echoes depends on the difference in acoustic impedance of the discontinuous surface at which ultrasound is reflected. When the transmitted ultrasound pulse is reflected at moving blood flow or a surface such as heart wall, the echo signal undergoes a frequency shift depending on the velocity component of the moving object in the ultrasound transmission direction, due to the Doppler effect.

A variety of ultrasound probes can be used as the ultrasound probe 1. For example, the ultrasound probe 1 may be a one-dimensional ultrasound probe including a plurality of piezo transducer elements arranged in a row. Another example of the ultras end probe 1 may be a one-dimensional ultrasound probe including a plurality of piezo transducer elements arranged in a row and mechanically swung. Yet another example of the ultrasound probe 1 may be a two-dimensional ultrasound probe including a plurality of piezo transducer elements two-dimensionally arranged in a grid.

The monitor 2 displays, for example, graphical user interfaces (GUIs) for the operator of the ultrasonic diagnostic apparatus to input settings and requests using the input device 3, and ultrasonic image data generated in the apparatus body 10. The monitor 2 is an example of the display unit.

The input device 3 includes, for example, a mouse, a keyboard, a button, a panel switch, a touch command screen, a foot switch, a trackball, and/or a joystick, and accepts settings and requests from the operator of the ultrasonic diagnostic apparatus to transfer the accepted settings and requests to the apparatus body 10.

The biological signal measuring device 4 acquires a periodic biological signal f the subject P. The biological signal measuring device 4 successively acquires biological signals of the subject P and transmits the acquired signals to the apparatus body 10. The biological signal measuring device 4 in the present embodiment is an electrocardiograph and acquires an electrocardiographic signal of the subject P as a biological signal of the subject P. The biological signal may be any signal in which periodicity can be recognized when evaluated in time series and from which a particular time phase can be extracted. Examples other than the electrocardiographic signal include a pulse wave signal and a phonocardiography signal. In the present embodiment, the biological signal measuring device 4 is separate from the apparatus body 10. The biological signal measuring device 4, however, may not be a separate unit. The biological signal measuring device 4 is an example of the acquisition circuit.

The apparatus body 10 is an apparatus that generates ultrasonic image data based on an echo signal produced from an echo received by the ultrasound probe 1. The apparatus body 10 includes, as illustrated in FIG. 1, the transmitter 11, a receiver 12, a signal processor 13, an image generator 14, an image memory 15, an internal storage 16, and a controller 17.

The transmitter 11 is a transmitting circuit that controls transmission directivity in ultrasound transmission. Specifically, the transmitter 11 includes a rate pulse generator, a transmission delay unit, and a transmission pulser to supply a drive signal to the ultrasound probe 1. The rate pulse generator repeatedly generates a rate pulse for forming transmission ultrasound at a predetermined pulse repetition frequency (PRF). The rate pulses pass through the transmission delay unit to apply voltage to the transmission pulser with different delay times. That is, the transmission delay unit provides a rate pulse generated by the rate pulse generator with a transmission delay time for each transducer element necessary for focusing ultrasound produced from the ultrasound probe 1 into a beam to determine transmission directivity. The transmission pulser applies a drive signal (drive pulse) to the ultrasound probe 1 at the timing based on such a rate pulse. The transmission direction or the transmission delay time is stored in the internal storage 16 described later. The transmitter 11 refers to the internal storage 16 to control transmission directivity.

The drive pulse is transmitted from the transmission pulser to a transducer element in the ultrasound probe 1 through a cable and then converted from an electrical signal into mechanical vibration in the transducer element. This mechanical vibration is transmitted as ultrasound in the inside of the body. Ultrasound having transmission delay times different among the transducer elements converges to propagate in a predetermined direction. The transmission delay unit adjusts the transmission direction from the transducer element surface as desired, by changing the transmission delay time applied to each rate pulse. The transmitter 11 provides transmission directivity by controlling the number and positions (transmit aperture) of transducer elements used for transmission of an ultrasonic beam as well as the transmission delay times in accordance with the positions of the transducer elements that form the transmit aperture. For example, the transmission delay unit of the transmitter 11 controls the position of the focus point (transmission focus) in the depth direction of ultrasound transmission, by applying a transmission delay time to each rate pulse generated by the rate pulse generator.

The transmitter 11 has a function capable of instantaneously changing a transmission frequency, a transmission drive voltage, and the like to execute a predetermined scan sequence, based on an instruction from the controller 17 described later. In particular, a transmission drive voltage is changed by a linear amplifier-type oscillator capable of instantaneously switching its values, or by a mechanism of electrically switching a plurality of power supply units.

The echo of ultrasound transmitted by the ultrasound probe 1 reaches the transducer elements in the ultrasound probe 1 and is then converted from mechanical vibration into an electrical signal (echo signal) in the transducer elements to be input to the receiver 12.

The receiver 12 is a receiving circuit that controls reception directivity in ultrasound reception. Specifically, the receiver 12 includes a preamplifier, an analog-to-digital (A/D) converter, a reception delay unit, and an adder to perform various processing on the echo signal received from the ultrasound probe 1 and generate echo data. The preamplifier amplifies the echo signal for each channel and performs gain correction processing. The A/D converter converts the gain-corrected echo signal into a digital signal. The reception delay unit applies a reception delay time necessary for determining reception directivity for each channel. The adder adds the echo signals (digital signals) having the reception delay times to generate echo data. The adding processing by the adder enhances the echo component from the direction corresponding to the reception directivity of the echo signals. The reception direction or the reception delay time is stored in the internal storage 16 described later. The receiver 12 refers to the internal storage 16 to control reception directivity. The receiver according to the first embodiment may perform parallel simultaneous reception.

The signal processor 13 is a processor that performs various signal processing on the echo data generated by the receiver 12 from echo signals. The signal processor 13 performs logarithmic amplification, envelope detection, and other processing on the echo data received front the receiver 12 to generate data (B mode data) representing the signal intensity for each sample point by brightness.

The signal processor 13 also generates data (Doppler data) by extracting motion information based on the Doppler effect of a moving object from the echo data received by the receiver 12 at each sample point in a scanned region. Specifically, the signal processor 13 generates Doppler data as motion information of a moving object, by extracting average velocity, variance, power value, and the like at each sample point. As used herein, the moving object is, for example, bloodstream, tissue such as heart wall, and contrast medium.

Here, the ultrasonic diagnostic apparatus according to the first embodiment is an apparatus capable of conducting elastography which measures the stiffness of biological tissue and visualizes the distribution of the measured stiffness. For example, the ultrasonic diagnostic apparatus according to the first embodiment conducts elastography by applying acoustic radiation force to produce displacement in biological tissue.

That is, the transmitter 11 according to the first embodiment allows the ultrasound probe 1 to transmit a push pulse (displacement-inducing burst wave) for producing displacement by shear waves caused by acoustic radiation force. The transmitter 11 according to the first embodiment then allows the ultrasound probe 1 to transmit a tracking pulse (observation pulse) multiple times for observing the displacement produced by the push pulse in each of plurality of scan lines in a scanned region. The tracking pulse is transmitted to observe the propagation speed of the shear wave generated by the push pulse at each sample point in the scanned region. In general, the tracking pulse is transmitted multiple times to each scan line in the scanned region. The receiver 12 generates echo data from the echo signal of the tracking pulse transmitted in each scan line in the scanned region.

The signal processor then analyses the echo data of the tracking pulse transmitted multiple times in each scan line in the scanned region to calculate stiffness distribution information indicating the distribution of stiffness of the scanned region. For example, the signal processor 13 generates stiffness distribution information of the scanned region by measuring the propagation speed of the shear wave produced by the push pulse at a sample point.

For example, the signal processor 13 analyzes the frequency of echo data of the tracking pulse. The signal processor 13 thus generates motion information (tissue Doppler data) over a plurality of time phases at each of a plurality of sample points of a scan line. The signal processor 13 then time-integrates velocity components of tissue Doppler data in a plurality of time phases obtained at each of the sample points of a scan line. The signal processor 13 thus calculates displacement at each of the sample points of a scan line over a plurality of time phases. The signal processor 13 then obtains a time at which displacement is largest at each sample point. The signal processor 13 then acquires the time at which the largest displacement is obtained at each sample point, as the shear wave arrival time at each sample point. The signal processor 13 then calculates the propagation speed of shear wave at each sample point by spatial differentiation of the shear wave arrival time at each sample point. The "propagation speed of shear wave" is hereinafter referred to as "shear wave speed".

The signal processor 13 then maps the color-coded shear wave speed to the corresponding sample point to generate stiffness distribution information. The shear wave speed is great for hard tissue, and the shear wave speed is small for soft tissue. That is, the greater the shear wave speed is, the greater the value indicating the tissue stiffness (elastic modulus) is. The shear wave speed may be calculated by the signal processor 13 detecting the correlation of tissue displacement between adjacent scan lines, rather than based on the time at which displacement is largest at each sample point.

The signal processor 13 may calculate the Young's modulus or shear modulus from the shear wave speed and generate stiffness distribution information from the calculated Young's modulus or shear modulus. Displacement, shear wave speed, Young's modulus, and shear modulus are physical quantities related to stiffness of biological tissue. Displacement, shear wave speed, and others are also physical quantities related to motion of biological tissue.

The shear wave produced by one transmission of a push pulse attenuates with propagation. When it is intended that the shear wave speed be observed over a wide region, the shear wave produced by a push pulse transmitted in a particular scan line attenuates with propagation and subsequently becomes unable to be observed at a sufficient distance from the transmission position of the push pulse.

In such a case, it is necessary to transmit a push pulse at a plurality of positions in the azimuth direction. For example, a region of interest (ROI) is divided into a plurality of regions along the azimuth direction. The transmitter 11 transmits push pulses at different scan line positions to produce shear waves, before transmitting and receiving tracking pulses in each region (hereinafter referred to as a divided region). In doing so, the transmission position of a push pulse is typically set in the vicinity of each divided region. When the number of simultaneous parallel receptions is limited to a few, the transmitter 11 successively performs, for each of a plurality of divided regions along the azimuth direction, the processing of transmitting a tracking pulse multiple times in each scan line of the divided region, after transmitting a push pulse. For example, the transmitter 11 transmits and receives tracking pulses after transmitting a push pulse in each of a plurality of divided regions.

The image generator 14 is a processor that generates ultrasonic image data from data generated by the signal processor 13. The image generator 14 generates B mode image data representing the intensity of echo by brightness, from the B mode data generated by the signal processor 13. The image generator 14 also generates Doppler image data representing moving object information from the Doppler data generated by the signal processor 13. The Doppler image data is velocity image data, variance image data, power image data, or image data of a combination thereof.

The image generator 14 also generates stiffness image data representing the stiffness of biological tissue in color, from the stiffness distribution information generated by the signal processor 13. For example, the image generator 14 generates, as stiffness image data, shear wave speed image data in which a pixel value corresponding to the shear wave speed at each point in the scanned region is allocated to the point.

Here, in general, the image generator 14 converts a scan line signal train in ultrasound scanning into a scan line signal train in a video format typically for televisions (scan conversion) to generate display ultrasonic image data. Specifically, the image generator 14 generates display ultrasonic image data by performing coordinate transformation in accordance with the format of ultrasound scanning by the ultrasound probe 1. The image generator 14 performs various image processing in addition to scan conversion, for example, image processing for regenerating a brightness mean value image (smoothing process) and image processing using a differential filter in an image (edge enhancing process), using a plurality of image frames after scan conversion. The image generator 14 combines supplementary information (for example, character information of parameters, scales, body marks) with the ultrasonic image data.

That is, the 13 mode data, the Doppler data, and the stiffness distribution information are ultrasonic image data before scan conversion, and the data generated by the image generator 14 is display ultrasonic image data after scan conversion.

The image memory 15 is a memory storing display image data generated by the image generator 14. The image memory 15 may also store data generated by the signal processor 13. The B mode data, the Doppler data, and the stiffness distribution information stored in the image memory 15 can be invoked, for example, by the operator after diagnosis and passed through the image generator 14 to produce display ultrasonic image data.

The internal storage 16 is a memory storing a control program for performing ultrasound transmission/reception, image processing, and display processing, diagnostic information (for example, patient ID, the doctor's observation), and a variety of data such as diagnosis protocols and body marks. The internal storage 16 is also used for saving image data stored in the image memory 15, as necessary. The data stored in the internal storage 16 can be transferred to an external device through a not-illustrated interface.

The controller 17 centrally controls the processing in the ultrasonic diagnostic apparatus. Specifically, the controller 17 controls the processing of the transmitter 11, the receiver 12, the signal processor 13, and the image generator 14, based on the settings and requests input from the operator through the input device 3, and a variety of control programs and data read from the internal storage 16. The controller 17 also performs control such that the display ultrasonic image data stored in the image memory 15 appears on the monitor 2.

The transmitter 11, the receiver 12, and others included in the apparatus body 10 may be configured by hardware such as a processor (for example, a central processing unit (CPU), a micro processing unit (MPU), an integrated circuit) or may be configured by software program modules.

The overall configuration of the ultrasonic diagnostic apparatus according to the first embodiment has been described above. With such a configuration, the ultrasonic diagnostic apparatus according to the first embodiment performs a variety of processing described below to accurately measure the physical quantity related to stiffness of biological tissue.

Figure 2A:
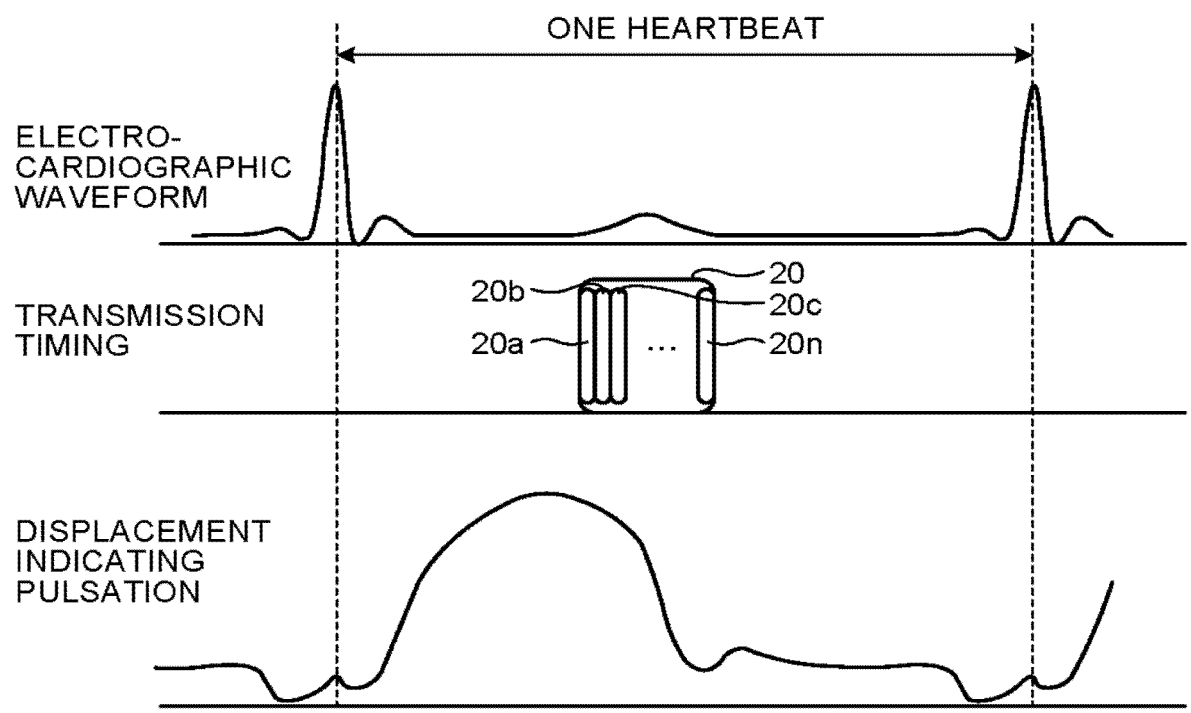
FIG. 2A is a diagram for explaining an example in which the physical quantity related to stiffness is measured by transmitting a push pulse and transmitting and receiving tracking pulses, in each of a plurality of divided regions of a region of interest (ROI), in one heartbeat.
Figure 2B:
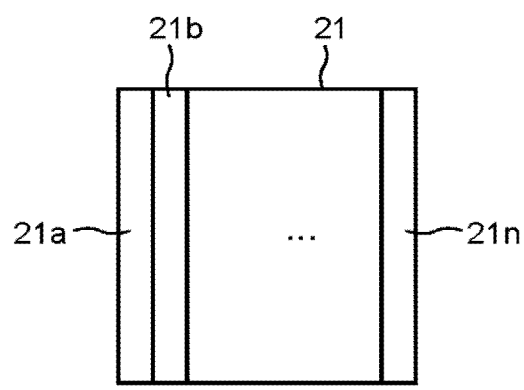
FIG. 2B is a diagram for explaining an example in which the physical quantity related to stiffness is measured by transmitting a push pulse and transmitting and receiving tracking pulses, in each of a plurality of divided regions of an ROI, in one heartbeat.

We will now explain a case where the physical quantity related to stiffness is measured by transmitting a push pulse and transmitting and receiving tracking pulses, in each of a plurality of divided regions in an ROI, in one heartbeat from a certain R wave to the next R wave. FIG. 2A and FIG. 2B are diagrams for explaining an example in which the physical quantity related to stiffness is measured by transmitting a push pulse and transmitting and receiving tracking pulses, in each of a plurality of divided regions of an ROI, in one heartbeat.

The example in FIG. 2A illustrates an example of the relation among the electrocardiographic waveform of an electrocardiographic signal of the subject, the amount of displacement at a predetermined part of the heart indicating the pulsation of the heart of the subject, and the timing at which a push pulse is transmitted and tracking pulses are transmitted and received in each of a plurality of divided regions of an ROI. The example in FIG. 2B illustrates an exemplary ROI 21 divided into a plurality of (n regions, where n is an integer equal to or greater than two) divided regions 21a to 21n.

In each of the divided regions 21a to 21n, the physical quantity related to stiffness is measured by transmitting a push pulse and transmitting and receiving tracking pulses. Blocks 20a to 20n illustrated in the example FIG. 2A are respective sets of a push pulse and tracking pulses transmitted in the divided regions 21a to 21n. The respective widths of the blocks 20a to 20n indicate the time in which a push pulse and tracking pulses are transmitted (transmission time) in the divided regions 21a to 21n. For example, the width of the block 20a indicates the transmission time for a push pulse and tracking pulses in the divided region 21a. This is applicable to the other blocks 20b to 20n. That is, the width of a block 20k (k=a, b, . . . , n) is the transmission time for a push pulse and tracking pulses in a divided region 21k. The width of the block 20 illustrated in FIG. 2A indicates the total of transmission times for a push pulse and tracking pulses in the blocks 203 to 20n.

Here, the time phase in which a push pulse and tracking pulses are transmitted in the divided region 21a differs from the time phase in which a push pulse and tracking pulses are transmitted in the divided region 21n. This may lead to poor accuracy of stiffness distribution information generated based on the physical quantity measured in the divided regions 21a to 21n.

The ultrasonic diagnostic apparatus according to the present embodiment therefore transmits a push pulse and tracking pulses in the same time phase in a plurality of divided regions to measure the physical quantity related to stiffness. The physical quantity related to stiffness thus can be obtained accurately.

Figure 3:
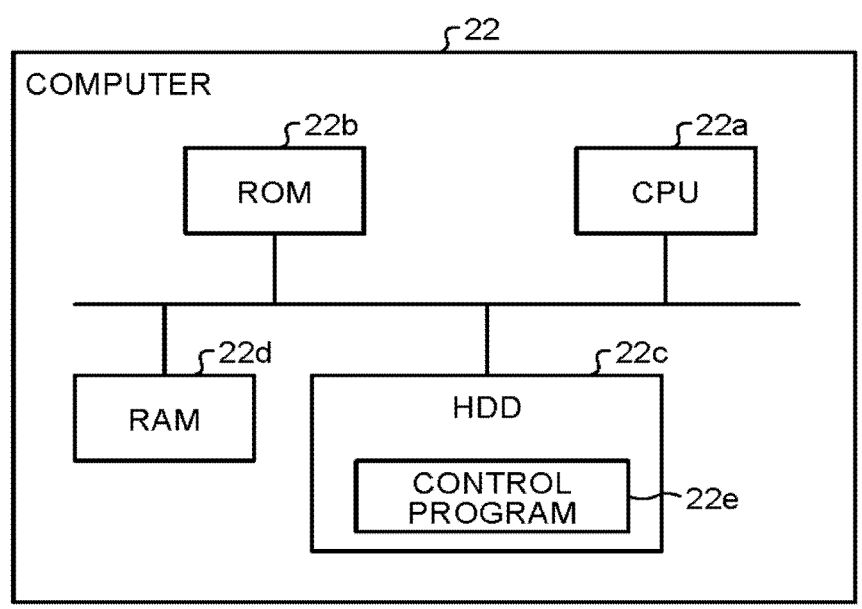
FIG. 3 is a diagram illustrating an example of the hardware configuration of a computer.

Returning to FIG. 1, the controller 17 includes a scan controller 171, a calculator 172, and a determiner 173. An example of the hardware of the controller 17 is a computer. A hardware configuration of such a computer will be described. FIG. 3 is a diagram illustrating an example of the hardware configuration of a computer. As illustrated in the example in FIG. 3, a computer 22 includes a central processing unit (CPU) 22a, a read only memory (ROM) 22b, a hard disk drive (HDD) 22c, and a random access memory (RAM) 22d. The CPU 22a, the ROM 22b, the HDD 22c, and the RAM 22d are connected through a bus. Basic programs such as an operating system (OS) are stored in the ROM 22b. A control program 22e is stored in the HDD 22c in advance.

The CPU 22a reads the control program 22e from the HDD 22c for execution. In doing so, the CPU 22a temporarily stores various data used for processing into the RAM 22d to execute the control program 22e. The CPU 22a executes the control program 22e in this manner to virtually implement the scan controller 171, the calculator 172, and the determiner 173 in the controller 17.

Figure 4:
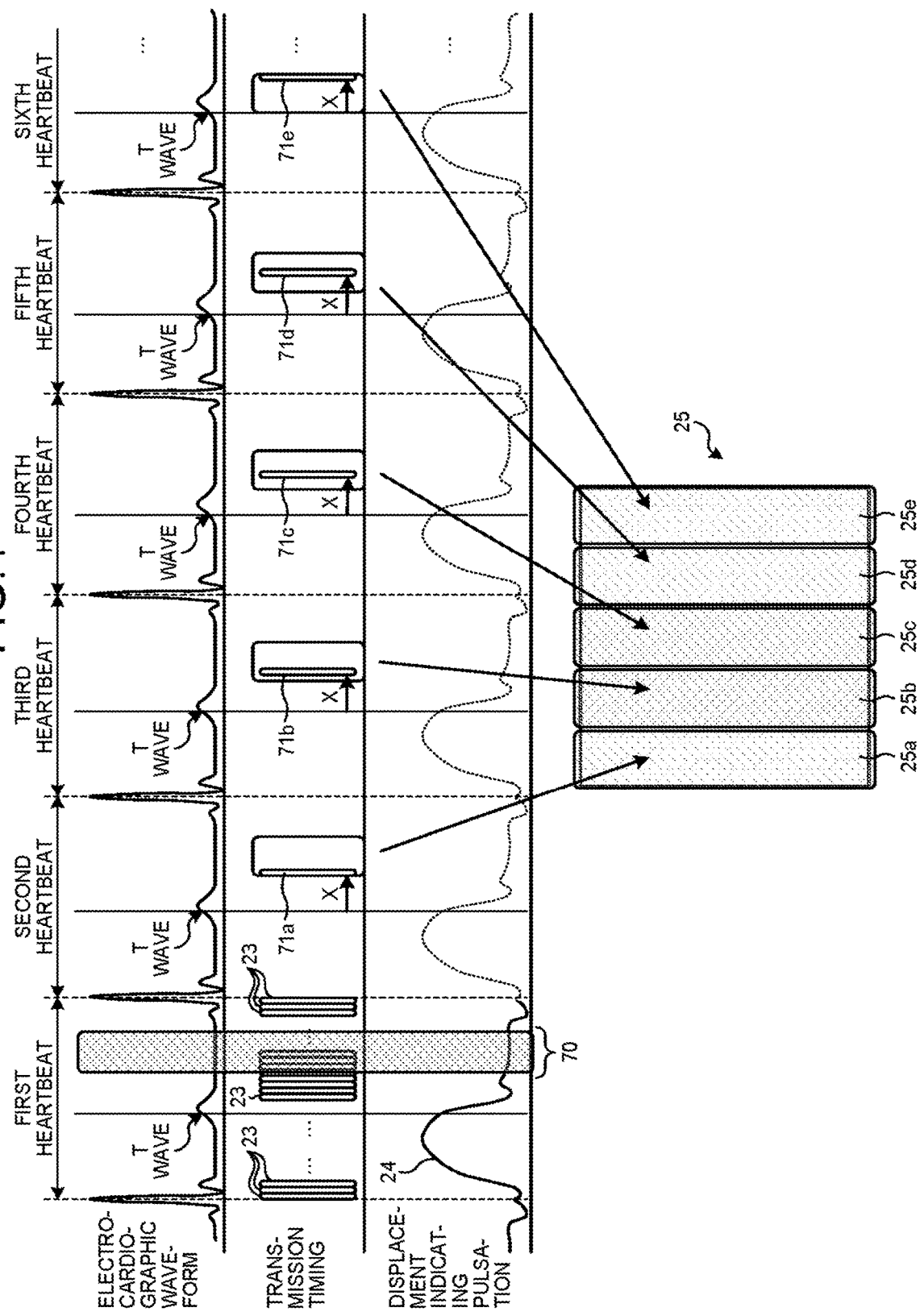
FIG. 4 is a diagram for explaining an example of the pre-scan and the main scan.

The scan controller 171 executes a pre-scan and a main scan. In a broad sense, the scan in the present embodiment includes, for example, acquisition of echo data of one frame through transmission and reception of converging wave multiple times and acquisition of echo data of one frame through transmission and reception of plane wave once. FIG. 4 is a diagram for explaining an example of the pre-scan and the main scan.

The example in FIG. 4 illustrates the relation among the electrocardiographic waveform of an electrocardiographic signal of the subject P acquired by the biological signal measuring device 4, the transmission timing of a push pulse and tracking pulses, and the displacement indicating the pulsation of the heart of the subject P.

The example in FIG. 4 illustrates the electrocardiographic waveform from the first heartbeat to the sixth heartbeat. Here, the heartbeat at which the pre-scan is performed is considered as the first heartbeat. In the example in FIG. 4, the scan controller 171 controls the processing of the transmitter 11, the receiver 12, the signal processor 13, and the image generator 14 such that the pre-scan is executed in the first heartbeat and that the main scan is executed in each of the second to sixth heartbeats using the result obtained in the pre-scan.

For example, the scan controller 171 controls the transmitter 11 such that tracking pulses are transmitted from the ultrasound probe 1 to a particular portion in an ROI 25, during the transmission time indicated by the width of each of blocks 23 continuous in a row on the whole in the first heartbeat, as illustrated in the example in FIG. 4. In one block 23, for example, a plurality of tracking pulses are transmitted. The width of one block 23 indicates the transmission time for a plurality of tracking pulses. The scan controller 171 also controls the receiver 12 so as to generate echo data at a predetermined position in the ROI to which tracking pulses are transmitted in the first heartbeat. The scan controller 171 may control the receiver 12 so as to generate echo data at a plurality of positions in the ROI to which tracking pulses are transmitted in the first heartbeat. The scan controller 171 thus executes the pre-scan for generating echo data by transmitting tracking pulses, in the first heartbeat. That is, the pre-scan includes transmission and reception of tracking pulses. The reception of tracking pulses refers to reception of echoes of tracking pulses. The pre-scan is a scan executed multiple times in succession.

The calculator 172 calculates an indicator related the motion of biological tissue in the subject P, based on echo data obtained through the pre-scan for the subject P. The indicator related to the motion of biological tissue includes displacement and velocity of biological tissue.

For example, as illustrated in the example in FIG. 4, the calculator 172 calculates displacement 24 indicating the pulsation of the heart of the subject P in the first heartbeat, from echo data obtained through the pre-scan. For example, the calculator 172 analyzes the frequency of the echo data to generate motion information (tissue Doppler data) and time-integrates the velocity component of tissue Doppler data to calculate the displacement 24 indicating the pulsation of the heart of the subject P in the first heartbeat. The calculator 172 may calculate an indicator related to the motion of biological tissue, such as displacement, through speckle tracking between ultrasonic images. Alternatively, the calculator 172 may calculate up to the velocity component of tissue Doppler data, rather than calculating up to the displacement. In the example in FIG. 4, in the second to sixth heartbeats, the displacement indicating the pulsation of the heart is denoted by a dashed line. The displacement denoted by the dashed line, however, is not the one calculated by the calculator 172 but merely indicates that the displacement 24 calculated in the first heartbeat is periodically repeated also in the second to sixth heartbeats.

The determiner 173 specifics at least one time phase in one cycle of the electrocardiographic signal of the subject F acquired by the biological signal measuring device 4 during the pre-scan, in the first heartbeat, based on the displacement 24 in the first heartbeat calculated by the calculator 172. Here, the determiner 173 specifies, for example, a time phase 70 in which the amount of change in displacement indicating pulsation of the heart in a predetermined period is equal to or smaller than a predetermined threshold. The determiner 173 then calculates a time phase difference between the specified time phase 70 and a time phase in which the electrocardiographic signal acquired during the pre-scan exhibits a distinctive change. As used herein, the time phase exhibiting a distinctive change refers to, for example, a time phase exhibiting a change corresponding to the T wave. That is, the determiner 173 calculates the time from the T wave to the time phase 70. The predetermined period mentioned above refers to, for example, a period longer than the transmission time for a push pulse and tracking pulses in each of the second to sixth heartbeats.

The processing of executing a pre-scan by the scan controller 171, the processing of calculating displacement by the calculator 172, and the processing of specifying the time phase 70 and calculating a time phase difference by the determiner 173 are performed, for example, in the first heartbeat illustrated by the example in FIG. 4 or by the time immediately after the second heartbeat starts.

In the second heartbeat, the determiner 173 determines the timing of a main scan for the subject P, based on the specified time phase 70 and the electrocardiographic signal in the second heartbeat of the subject P acquired by the biological signal measuring device 4. More specifically, the determiner 173 determines the timing of a main scan for the subject P, based on the time phase difference calculated in the first heartbeat and the time phase in which the electrocardiographic signal acquired by the biological signal measuring device 4 in the second heartbeat subsequent to the pre-scan exhibits a change that is substantially identical to the distinctive change. As used herein, the time phase exhibiting a substantially identical change is equivalent to the time phase exhibiting a change corresponding to the T wave. We will now describe a case where the time phase difference calculated in the first heartbeat is a time X. In this case, the determiner 173 determines, as the timing for performing a main scan, the timing when the time X has passed since the T wave indicated by the electrocardiographic waveform in the second heartbeat.

The scan controller 171 then controls the transmitter 11 such that transmission of push pulse from the ultrasound probe 1 to the vicinity of a divided region 25a of the ROI 25 illustrated in the example in FIG. 4 is started at the timing determined by the determiner 173. In the second heartbeat, the scan controller 171 also controls the transmitter 11 such that tracking pulses are transmitted from the ultrasound probe 1 to the divided region 25a immediately after transmission of the push pulse is finished. A block 71a illustrated in the example in FIG. 4 denotes a set of a push pulse and tracking pulses in the second heartbeat. The width of the block 71a indicates the transmission time for a push pulse and tracking pulses in the second heartbeat. In the second heartbeat, the scan controller 171 controls the receiver 12 so as to generate echo data of the divided region 25a to which tracking pulses are transmitted. The scan controller 171 thus executes a main scan for generating echo data of the divided region 25a by starting transmission of a push pulse and tracking pulses at the timing when the time has passed since the T wave, in the second heartbeat. That is, the scan controller 171 executes a main scan in the time phase in which the amount of change in displacement indicating the pulsation of the heart in a predetermined period is equal to or smaller than a predetermined threshold in the second heartbeat. The main scan is thus executed at the timing when the motion of the heart is small.

The determiner 173 then determines the timing when the time X has passed since the T wave indicated by the electrocardiographic waveform, as the timing for performing a main scan, in the same manner in the third to sixth heartbeats. The scan controller 171 executes a main scan for generating respective echo data of the divided regions 25b to 25e by starting transmission of a push pulse and tracking pulses at the timing determined by the determiner 173, in the same manner, also in the third to sixth heartbeats. Blocks 71b to 71e illustrated in the example in FIG. 4 indicate respective sets of a push pulse and tracking pulses in the third to sixth heartbeats, and the widths of the blocks 71b to 71e indicate the transmission time for a push pulse and tracking pulses in the third to sixth heartbeats. That is, the main scan includes transmission of a push pulse and transmission and reception of tracking pulses.

Here, in the present embodiment, the echo data obtained in the main scan in the second to sixth heartbeats is data captured at the same timing, that is, data captured in the same time phase. The echo data obtained in the main scan in the second to sixth heartbeats is data captured at the timing when there are few changes in displacement indicating the pulsation of the subject P, that is, data captured at the timing when the motion caused by pulsation is stable.

When echo data is obtained in the main scan in the second to sixth heartbeats, the scan controller 171 controls the signal processor 13 so as to generate stiffness distribution information of the divided region 25a, based on the echo data obtained in the main scan in the second heartbeat. Similarly, the scan controller 171 controls the signal processor 13 so as to generate respective stiffness distribution information of the divided regions 25b to 25e, based on the respective echo data obtained in the main scan in the third to sixth heartbeats.

The scan controller 171 then controls the image generator 14 so as to generate stiffness image data based on the stiffness distribution information of the divided region 25a. Similarly, the scan controller 171 controls the image generator 14 so as to generate stiffness image data, based on the respective stiffness distribution information of the divided regions 25b to 25e.

The scan controller 171 then controls the image generator 14 so as to synthesize the respective stiffness image data of the divided regions 25a to 25e. Stiffness image data representing a single stiffness image of the ROI 25 is thus generated.

The scan controller 171 then allows the stiffness image of the ROI 25 represented by the generated stiffness image data to appear on the monitor 2.

As described above, the ultrasonic diagnostic apparatus according to the present embodiment generates respective stiffness distribution information of the divided regions 25a to 25e, based on the accurate echo data obtained at a timing when the motion caused by pulsation is stable, in the second to sixth heartbeats. The ultrasonic diagnostic apparatus according to the present embodiment thus can accurately obtain the physical quantity related to stiffness.

Figure 5:
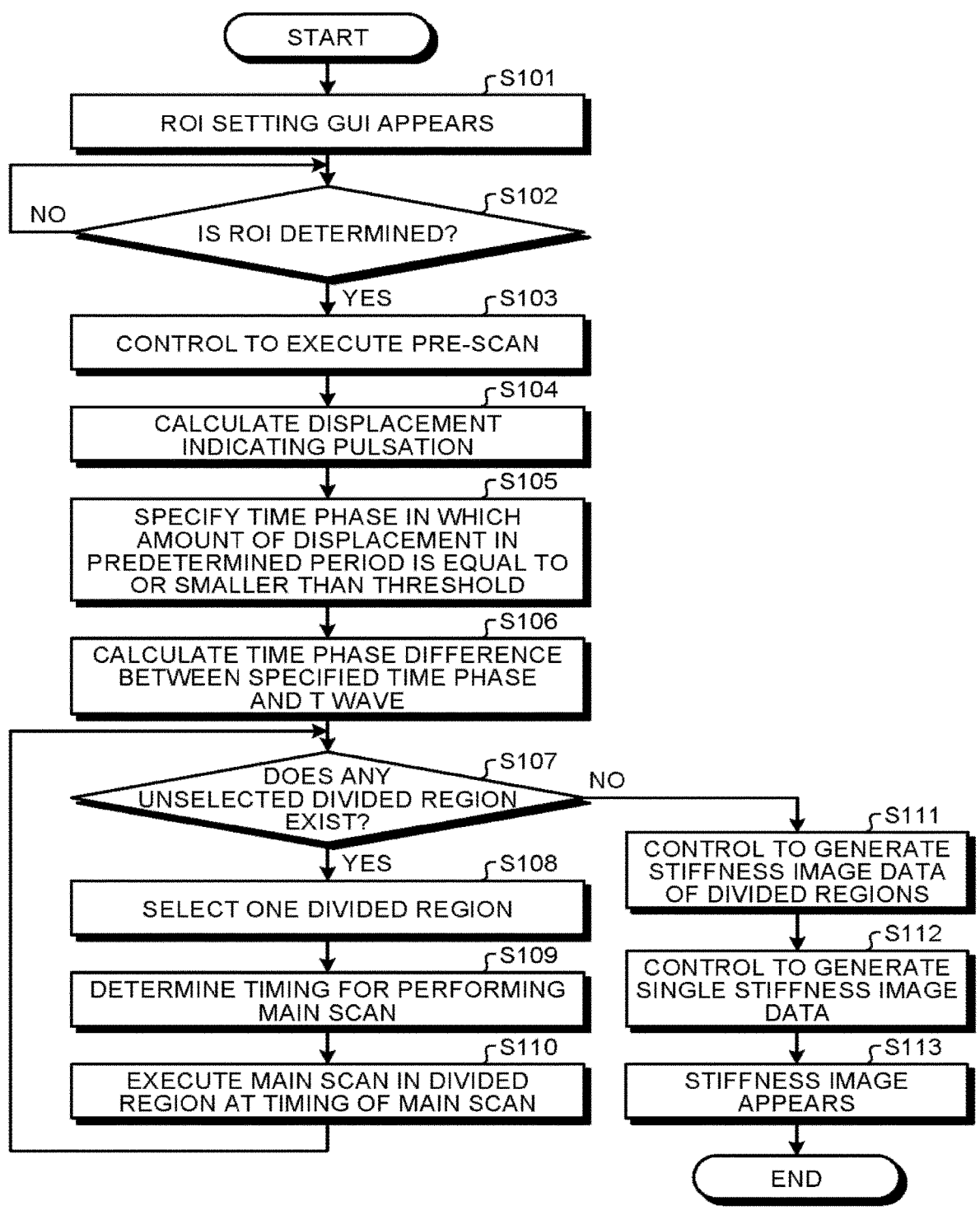
FIG. 5 is a flowchart for explaining an example of the stiffness image generating process according to the first embodiment.

FIG. 5 is a flowchart for explaining an example of stiffness image generating process according to the first embodiment. This stiffness image generating process is performed when a start instruction to start a stiffness image generation mode for generating a stiffness image is accepted from the operator. The stiffness image generation mode is, for example, a mode for generating a stiffness image. As illustrated in FIG. 5, the scan controller 171 allows a graphical user interface (GUI) for setting an ROI (ROI setting GUI) to appear on the monitor 2 (step S101). The monitor 2 then displays, for example, an ROI that specifies a region for generating a stiffness image on the B mode image through scanning by the ultrasound probe 1. The size and the position of the ROI are preset, and the scan controller 171 accepts an instruction to change the size and/or the position of the ROI from the operator to change the size and/or the position of the ROI in accordance with the accepted instruction.

The can controller 171 then determines whether the ROI is determined (step S102). For example, the scan controller 171 determines whether the ROI is determined, depending on whether an instruction to determine the ROT is accepted from the operator. If the ROI is not determined (No at step S102), the scan controller 171 performs the determination at step S102 again.

On the other hand, if the ROI is determined (Yes at step S102), the scan controller 171 divides the determined ROI into a plurality of divided regions, calculates a transmission position of a push pulse corresponding to each divided region, and controls the transmitter 11 and the receiver 12 so as to execute a pre-scan in a certain heartbeat (the first heartbeat (also referred to as the start heartbeat)) indicated by the electrocardiographic waveform (step S103).

The calculator 172 then calculates displacement indicating the pulsation of the heart of the subject P in the first heartbeat, from the echo data obtained through the pre-scan (step S104).

The determiner 173 then specifies a time phase in which the amount of change in displacement indicating pulsation of the heart in a predetermined period is equal to or smaller than a predetermined threshold, based on the calculated displacement in the first heartbeat (step S105).

The determiner 173 then calculates the time phase difference between the specified time phase and the time phase in which the electrocardiographic signal acquired during the pre-scan exhibits a distinctive change (the time phase exhibiting a change corresponding to the T wave) (step S106).

The determiner 173 then determines whether any unselected divided region (a divided region not selected at step S108 described later) exists among a plurality of divided regions (step S107).

If any unselected divided region exists (Yes at step S107), the scan controller 171 selects one unselected divided region (step S108). The determiner 173 then determines the timing when the time X has passed since the T wave, as the timing for performing a main scan (step S109). The scan controller 171 then executes a main scan in the divided region selected at step S109, at the timing of the main scan determined by the determiner 173 (step S110). The process then returns to step S107. For example, at step S110, the scan controller 171 controls the transmitter 11 such that transmission of a push pulse from the ultrasound probe 1 to the vicinity of the selected divided region is started at the timing when the time X has passed since the T wave indicated by the electrocardiographic waveform. At step S110, the scan controller 171 controls the transmitter 11 such that tracking pulses are transmitted from the ultrasound probe 1 to the divided region immediately after the transmission of a push pulse is finished. At step S110, the scan controller 171 controls the receiver 12 so as to generate echo data of the divided region to which tracking pulses are transmitted.

On the other hand, if no unselected divided region exists (No at step S107), the scan controller 171 controls the signal processor 13 so as to generate respective stiffness distribution information of the divided regions, based on respective echo data obtained in the main scan of the divided regions, and thereafter controls the image generator 14 so as to generate stiffness image data based on respective stiffness distribution information of the divided regions generated by the signal processor 13 (step S111).

The scan con roller 171 then controls the image generator 14 so as to synthesize respective stiffness image data of the divided regions to generate stiffness image data representing a single stiffness image of the ROI (step S112). The scan controller 171 then allows the stiffness image represented by the generated stiffness image data to appear on the monitor (step S113). The stiffness image generating process then ends. At step S113, the scan controller 171 may allow the measured values (for example, stiffness, shear wave speed, displacement) in the ROI of biological tissue of the subject P appear on the monitor 2.

The ultrasonic diagnostic apparatus according to the first embodiment has been described above. The ultrasonic diagnostic apparatus according to the first embodiment can accurately obtain the physical quantity related to stiffness as described above.

First Modification to First Embodiment

In the foregoing first embodiment, the calculator 172 calculates displacement and velocity as indicators related to the motion of biological tissue in the ROI, only in the heartbeat in which a pre-scan is performed. The present invention, however, is not limited to this embodiment. For example, the calculator 172 may calculate displacement and velocity of biological tissue in a divided region, based on the echo data of tracking pulses, also in a heartbeat in which a main scan is performed. In this case, the scan controller 171 may execute a main scan again in a divided region in which the displacement or velocity calculated in the main scan falls outside a predetermined range. Such an embodiment will be described as a first modification to the first embodiment.

Figure 6:
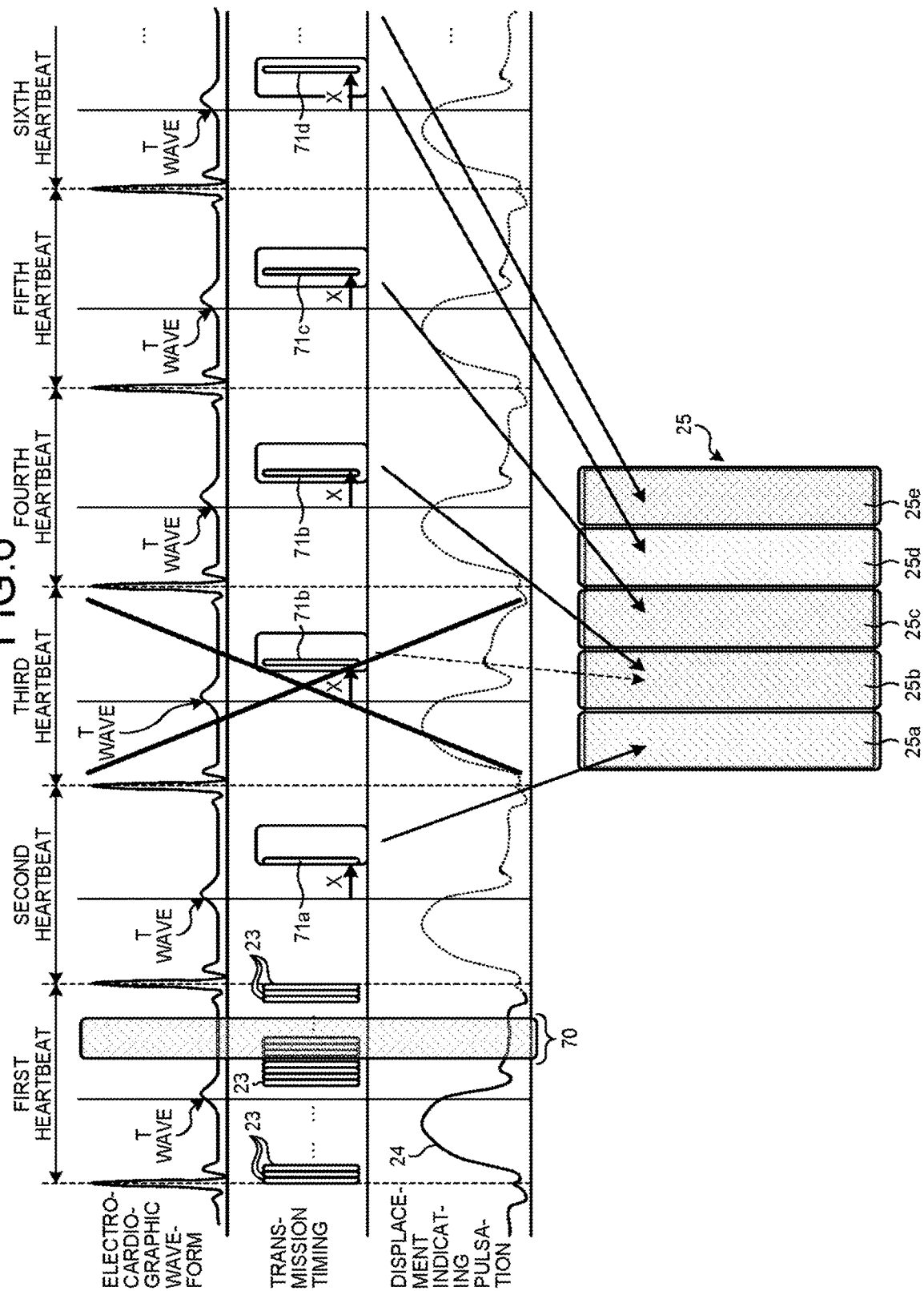
FIG. 6 is a diagram for explaining an example of a first modification to the first embodiment.

FIG. 6 is a diagram for explaining an example of the first modification to the first embodiment. As illustrated in the example in FIG. 6, when the displacement of biological tissue in a divided region 25b calculated by the calculator 172 falls outside a predetermined range in the third heartbeat, the scan controller 171 executes a main scan again in this divided region 25b in the fourth heartbeat. Such a main scan executed again is also referred to as preliminary imaging. Here, the predetermined range is, for example, a range equal to or greater than ($\alpha-\beta$) and equal to or smaller than ($\alpha+\beta$) where $\alpha$ is the displacement in the same time phase calculated by the calculator 172 in the pre-scan, and $\beta$ is a predetermined value. Alternatively, the predetermined range is a range in which the slope of the graph illustrating the displacement is approximately zero.

This processing invalidates the physical quantity related to stiffness of biological tissue in a divided region that is obtained through a main scan when there is such a large change in displacement of the pulsation of the heart of the subject P that an indicator calculated falls outside predetermined range. A stiffness image thus can be generated without using inaccurate physical quantity related to stiffness. That is, poor accuracy of a stiffness image can be eliminated or minimized.

If the displacement of biological tissue in a divided region calculated by the calculator 172 falls outside a predetermined range a predetermined number of times in succession (for example, four times for four heartbeats), the scan controller 171 allows a message to appear on the monitor 2 to indicate that the calculated displacement of biological tissue in a divided region falls outside a predetermined range a predetermined number of times in succession. In such a case, the scan controller 171 may control the transmitter 11 and the receiver 12 so as to automatically execute the preliminary imaging described above.

Second Modification to First Embodiment

In the first embodiment, a main scan is executed once in one cycle of the electrocardiographic signal. However, a main scan may be executed multiple times (for example, twice) in one cycle of the electrocardiographic signal. This modification can reduce the time required for the main scan as a whole.

Second Embodiment

The ultrasonic diagnostic apparatus according to a second embodiment will now be described. The same components as those in the first embodiment are denoted with the same reference signs and a description thereof may be omitted.

Figure 7:
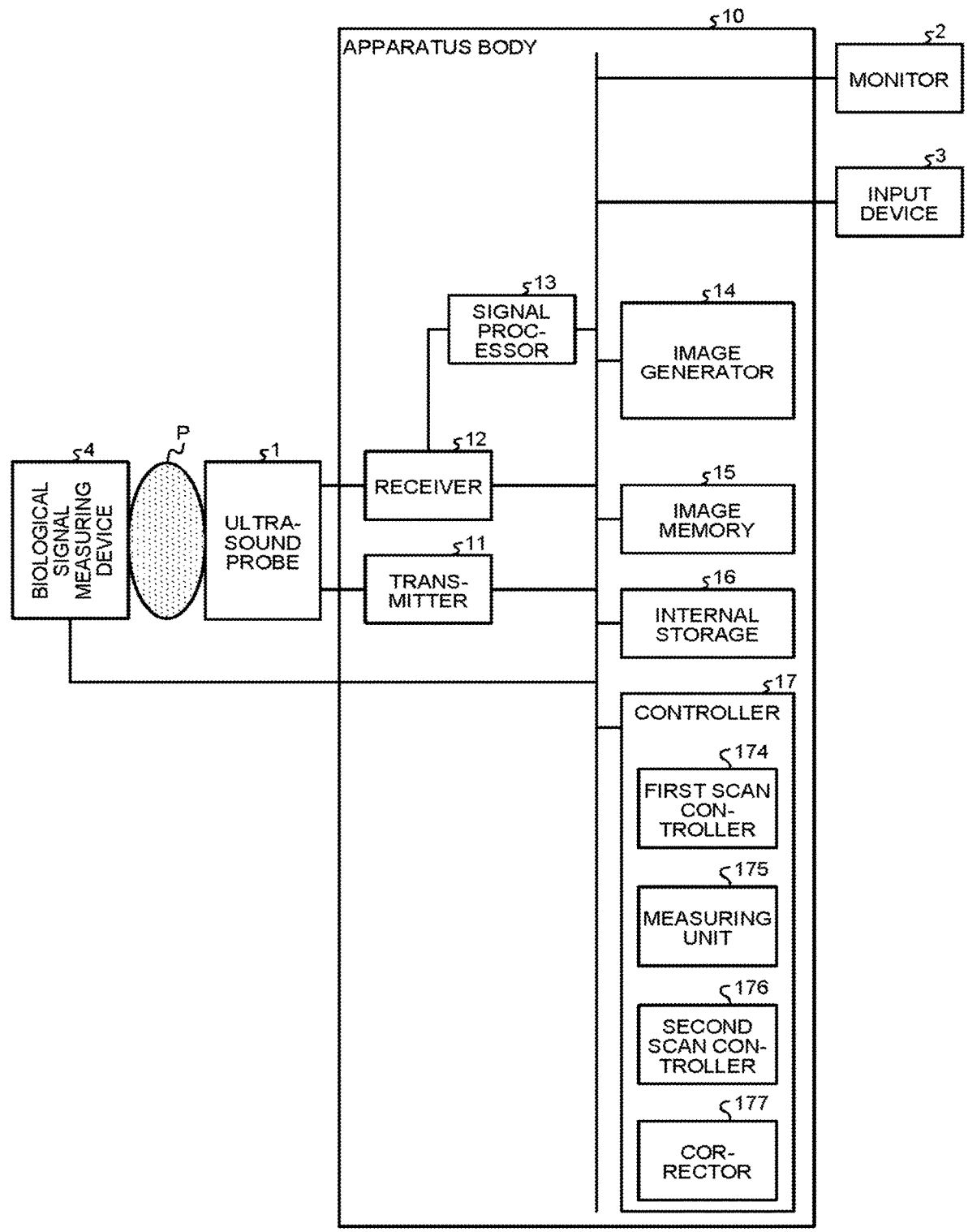
FIG. 7 is a block diagram illustrating a configuration example of the ultrasonic diagnostic apparatus according to a second embodiment.

FIG. 7 is a block diagram illustrating a configuration example of the ultrasonic diagnostic apparatus according to the second embodiment. As illustrated in FIG. 7, the ultrasonic diagnostic apparatus according to the second embodiment differs from the ultrasonic diagnostic apparatus according to the first embodiment in that the controller 17 includes a first scan controller 174, a measuring unit 175, a second scan controller 176, and a corrector 177, in place of the scan controller 171, the calculator 172, and the determiner 173 according to the first embodiment illustrated in FIG. 1. In the present embodiment, a pre-scan and a main scan are performed in a systole. However, a pre-scan and a main scan may be performed in a diastole.

Figure 9:
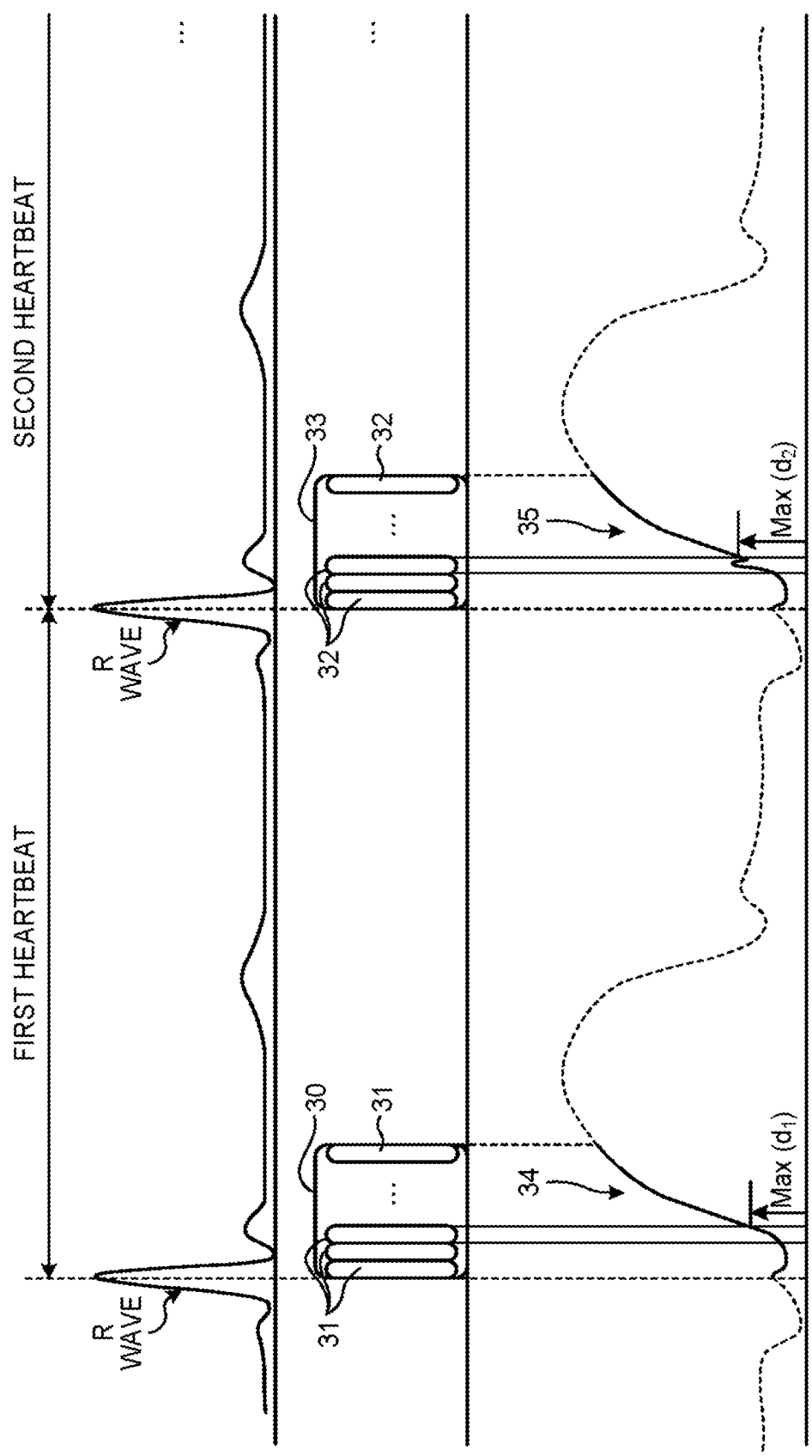
FIG. 9 is a diagram for explaining an example of the processing performed by the ultrasonic diagnostic apparatus according to the second embodiment.

The first scan controller 174 executes a pre-scan. FIG. 6 and FIG. 9 are diagrams for explaining an example of the processing performed by the ultrasonic diagnostic apparatus according to the second embodiment.

Figure 8:
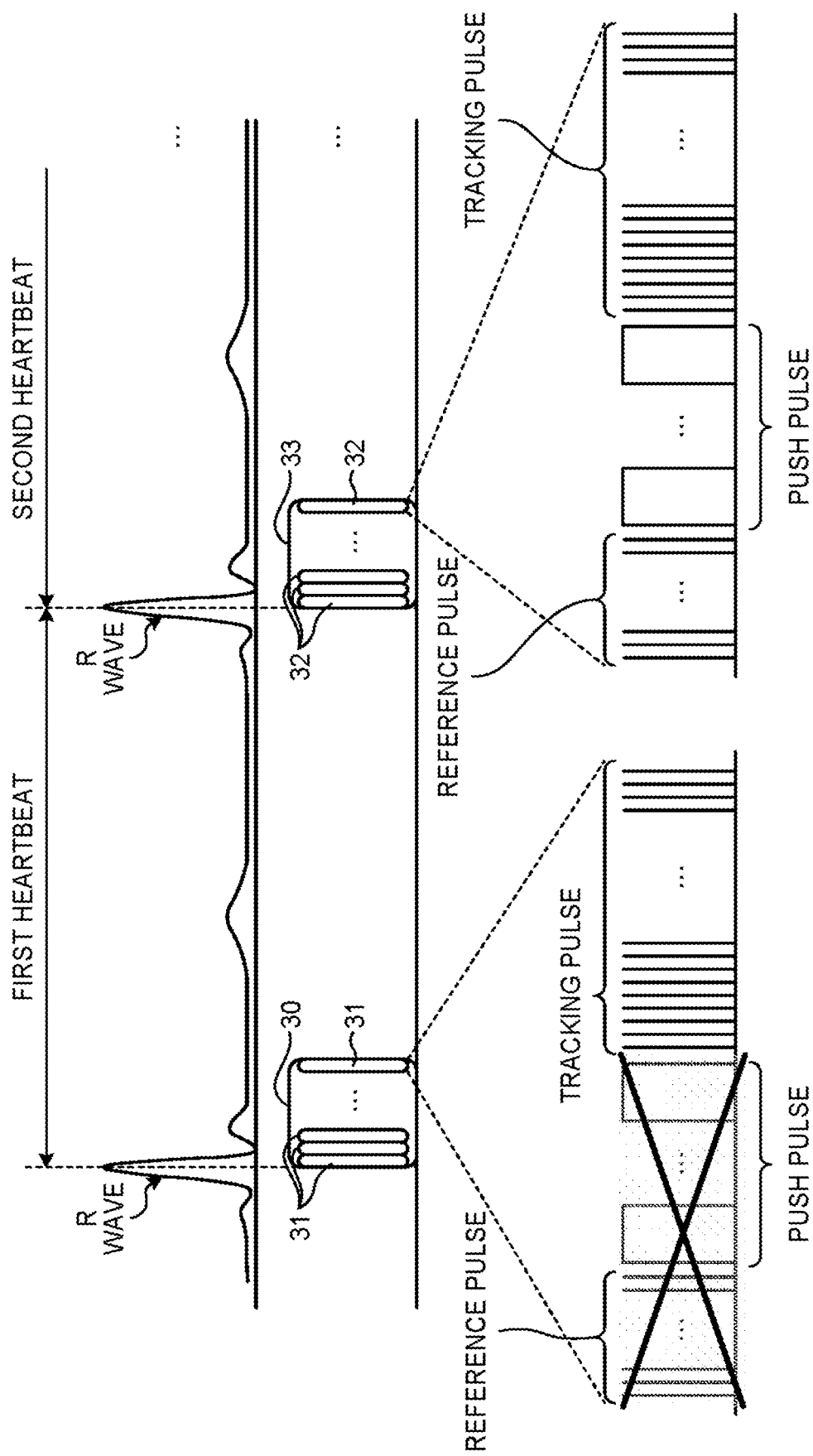
FIG. 8 is a diagram for explaining an example of the processing performed by the ultrasonic diagnostic apparatus according to the second embodiment.

As illustrated in the example in FIG. 8, in the first heartbeat, the first scan controller 174 controls the transmitter 11 such that tracking pulses are transmitted from the ultrasound probe 1 at the same or almost the same timing as the timing from the R wave at which tracking pulses are transmitted in the main scan. Here, in the main scan according to the second embodiment, in the second heartbeat, transmission of reference pulses, push pulses, and tracking pulses for each divided region is repeated the number of times corresponding to the number of divided regions. Such transmission of those pulses for each divided region is started at the timing of the R wave when the second heartbeat starts illustrated in the example in FIG. 8, a set of reference pulses, push pulses, and tracking pulses for each divided region is denoted by a block 32. That is, as illustrated in the example in FIG. 8, in a main scan, the block 32 is repeated the number of times corresponding to the number of divided regions. The width of one block 32 indicates the transmission time for reference pulses, push pulses, and tracking pulses for each divided region. A block 33 illustrated in the example in FIG. 8 represents all of the reference pulses, the push pulses, and the tracking pulses in the main scan that are equivalent to all of the blocks 32. The width of the block 33 indicates the transmission time for all of the reference pulses, the push pulses, and the tracking pulses in the main scan.

The first scan controller 174 controls the transmitter 11 such that tracking pulses are transmitted in the first heartbeat at the timing when the transmission time for reference pulses and push pulses in the main scan has passed since the R wave at the start of this heartbeat. The first scan controller 174 then controls the transmitter 11 such that transmission of a second tracking pulse group is started at the timing when the transmission time for reference pulses and push pulses has passed since transmission of the first tracking pulse group is completed. The first scan controller 174 performs transmission of the third and subsequent tracking pulse groups in the same manner. That is, the first scan controller 174 controls the transmitter 11 such that the transmission of tracking pulses is performed the number of times corresponding to the number of divided regions.

As illustrated in the example in FIG. 8, a block 31 represents tracking pulses transmitted for each divided region after an interval corresponding to the transmission time for reference pulses and push pulses in the main scan. That is, as illustrated in the example in FIG. 8, in the pre-scan, the block 31 is repeated the number of times corresponding to the number of divided regions. In one block 31, a tracking pulse is transmitted multiple times (a plurality of tracking pulses) after an interval corresponding to the transmission time for reference pulses and push pulses from the start timing of the block 31. The width of one block 31 indicates the transmission time for reference pulses and push pulses and the transmission time for tracking pulses in a main scan for each divided region. That is, the time indicated by the width of one block 31 is equal to the time indicated by the width of one block 32. A block 30 illustrated in the example in FIG. 8 represents all of the tracking pulses in the pre-scan that are equivalent to all of the blocks 31. The width of the block 30 indicates the total time of all the intervals in the pre-scan and the transmission times for tracking pulses in the pre-scan.

In the first heartbeat, the first scan controller 174 controls the receiver 12 so as to generate, for each divided region to which tracking pulses are transmitted, echo data of the divided region.

As described above, the first scan controller 174 executes a pre-scan for generating echo data by transmitting tracking pulses at the same timing as the timing when tracking pulses are transmitted in the main scan, in the first heartbeat. That is, the first scan controller 174 executes a pre-scan for biological tissue of the subject P by transmitting and receiving tracking pulses in a predetermined time phase in a first cycle, which is a cycle of the biological signal corresponding to the first heartbeat. As used herein, the predetermined time phase corresponds to the timing when an interval corresponding to the transmission time for reference pulses and push pulses has passed since the start timing of the block 31, in each of a plurality of blocks 31.

Next, the measuring unit 175 measures displacement indicating the pulsation of the heart of the subject P for each divided region, as a physical quantity related to motion of biological tissue of the subject P, based on the echo data obtained through the pre-scan in the first heartbeat.

For example, as illustrated in the example in FIG. 9, the measuring unit. 175 measures displacement 34 indicating the pulsation of the heart of the subject P in the first heartbeat, from ho data obtained through the pre-scan. For example, the measuring unit 175 analyses the frequency of the echo data to generate motion information (tissue Doppler data) and time-integrates the velocity component of the tissue Doppler data to measure the displacement 34 indicating the pulsation of the heart of the subject P in the first heartbeat. The measuring unit 175 may measure up to the velocity component of the tissue Doppler data, rather than measuring up to the displacement. In the example in FIG. 9, the displacement indicating pulsation of the heart is denoted by a dashed line. This indicates a measurement result supposing that tracking pulses are transmitted at the timing denoted by the dashed line to measure the displacement.

The second scan controller 176 then executes a main scan as described above, in the second heartbeat. For example, as illustrated in the example in FIG. 8, the second scan controller 176 controls the transmitter 11 such that the transmission of reference pulses from the ultrasound probe 1 to a divided region is started at the timing of the R wave when the second heartbeat starts. The second scan controller 176 also controls the receiver 12 so as to generate echo data of the divided region to which reference pulses are transmitted. The second scan controller 176 controls the transmitter 11 such that push pulses are transmitted from the ultrasound probe 1 to the vicinity of the divided region immediately after the transmission of reference pulses is finished. The second scan controller 176 controls the transmitter 11 such that tracking pulses are transmitted from the ultrasound probe 1 to the divided region immediately after the transmission of push pulses is finished. The second scan controller 17 controls the receiver 12 so as to generate echo data of the divided region to which tracking pulses are transmitted. The second scan controller 176 then repeatedly performs the processing as described above the number of times corresponding to the number of divided regions. As described above, the second scan controller 176 executes a main scan by transmitting reference pulses to generate echo data of reference pulses in a divided region and transmitting push pulses and tracking pulses to generate echo data of tracking pulses in the divided region, in the second heartbeat, the number of times corresponding to the number of divided regions. That is, the second scan controller 176 executes a main scan for biological tissue of the subject P by transmitting and receiving reference pulses transmitting push pulses, and transmitting and receiving tracking pulses after the transmission of push pulses a time phase that is substantially identical to the predetermined time phase, in a second cycle, which is a cycle of the biological signal corresponding to the second heartbeat. As used herein, the second cycle is a cycle that is different from the foregoing first cycle and later than the first cycle in time series. Reception of a reference pulse refers to reception of the echo of a reference pulse. Transmission and reception of reference pulses and transmission of push pulses may be performed in the first cycle.

Next, the measuring unit 175 calculates, for each divided region, displacement of biological tissue in the divided region, serving as intermediate data, based on the echo data of reference pulses obtained in the main scan in the second heartbeat, and generates stiffness distribution information based on the calculated displacement. The measuring unit 175 calculates, for each divided region, displacement of biological tissue in the divided region, serving as intermediate data, based on the echo data of tracking pulses obtained in the main scan in the second heartbeat, and generates stiffness distribution information based on the calculated displacement. The measuring unit 175 then subtracts, for each divided region, the stiffness distribution information generated based on the echo data of reference pulses from the stiffness distribution information generated based on the echo data of tracking pulses to generate new stiffness distribution information. The second scan controller 176 generates respective stiffness image data for all the divided regions, based on the respective new stiffness distribution information. The second scan controller 176 then synthesizes the respective stiffness image data of all the divided regions to generate stiffness image data representing a single stiffness image of the ROI. The second scan controller 176 then allows the stiffness image of the ROI represented by the generated stiffness image data to appear on the monitor 2.

Here, the corrector 177 corrects, for each divided region, the displacement of biological tissue in the divided region, which is intermediate data used when the measuring unit 175 generates stiffness distribution information based on the echo data of tracking pulses obtained in the main scan in the second heartbeat. For example, the displacement of biological tissue in a divided region serving as intermediate data is preferably the displacement of biological tissue caused by a push pulse alone. However, a component of pulsation (pulsation component) of the heart of the subject P may be included in the displacement of biological tissue in a divided region serving as intermediate data. The pulsation component is ten to a hundred times as large as displacement. The corrector 177 according to the present embodiment then eliminates this pulsation component from the displacement of biological tissue in the divided region serving as intermediate data, so that the displacement of biological tissue in the divided region serving as intermediate data is corrected to the displacement of biological tissue caused by a push pulse alone. Stiffness distribution information thus can be obtained accurately.

For example, we will describe, in the example in FIG. 9, correction of the displacement of biological tissue in a divided region, which is intermediate data used when stiffness distribution information is generated based on the echo data of tracking pulses corresponding to the third block 32 in chronological order among a plurality of blocks 32.

Here, a pulsation component, in the block 31 corresponding to the third block 32 in chronological order (the third block 31 in chronological order among a plurality of blocks 31) is denoted by d1. The pulsation component in the third block 32 in chronological order is denoted by d2. It is noted that d1 is also displacement measured by the measuring unit 175 based on the echo data of tracking pulses corresponding to the third block 31 in chronological order, and d2 is also displacement measured by the measuring unit 175 based on the echo data of reference pulses corresponding to the third block 32 in chronological order. The maximum value of the pulsation component d1 in the third block 31 in chronological order is denoted by Max(d1). The maximum value of the pulsation component d2 in the third block 32 in chronological order is denoted by Max(d2). The displacement measured by the measuring unit 175 based on the echo data of tracking pulses corresponding to the third block 32 in chronological order is denoted by d.

Here, d is the displacement including displacement by a push pulse and a pulsation component, and d1 is a pulsation component not including displacement by a push pulse. The corrector 177 then corrects the displacement d of biological tissue in the divided region serving as intermediate data to displacement dp of biological tissue caused by a push pulse alone, in accordance with Equation (1):

$$dp = d - M \cdot d1 \qquad (1)$$

where M=Max(d2)/Max(d1).

The corrector 177 thus corrects the result of transmission and reception of tracking pulses in the main scan with the result of transmission and reception of tracking pulses in the pre-scan. Here, the result of transmission and reception of tracking pulses in the pre-scan refers to, for example, the displacement of biological tissue calculated using the signal (echo signal) output from the ultrasound probe 1 receiving the echoes of tracking pulses transmitted to biological tissue of the subject P in the pre-scan. The result of transmission and reception of tracking pulses in the main scan refers to, for example, the displacement of biological tissue calculated using the signal (echo signal) output from the ultrasound probe 1 receiving the echoes of tracking pulses transmitted to biological tissue of the subject P in the main scan. The displacement of biological tissue is an example of the physical quantity related to motion of biological tissue.

Here, the measuring unit 175 generates stiffness distribution information as the physical quantity related to stiffness of biological tissue of the subject P, for each divided region, based on the corrected displacement as described above. That is, the measuring unit 175 generates stiffness distribution information based on the correction result by the corrector 177.

Figure 10:
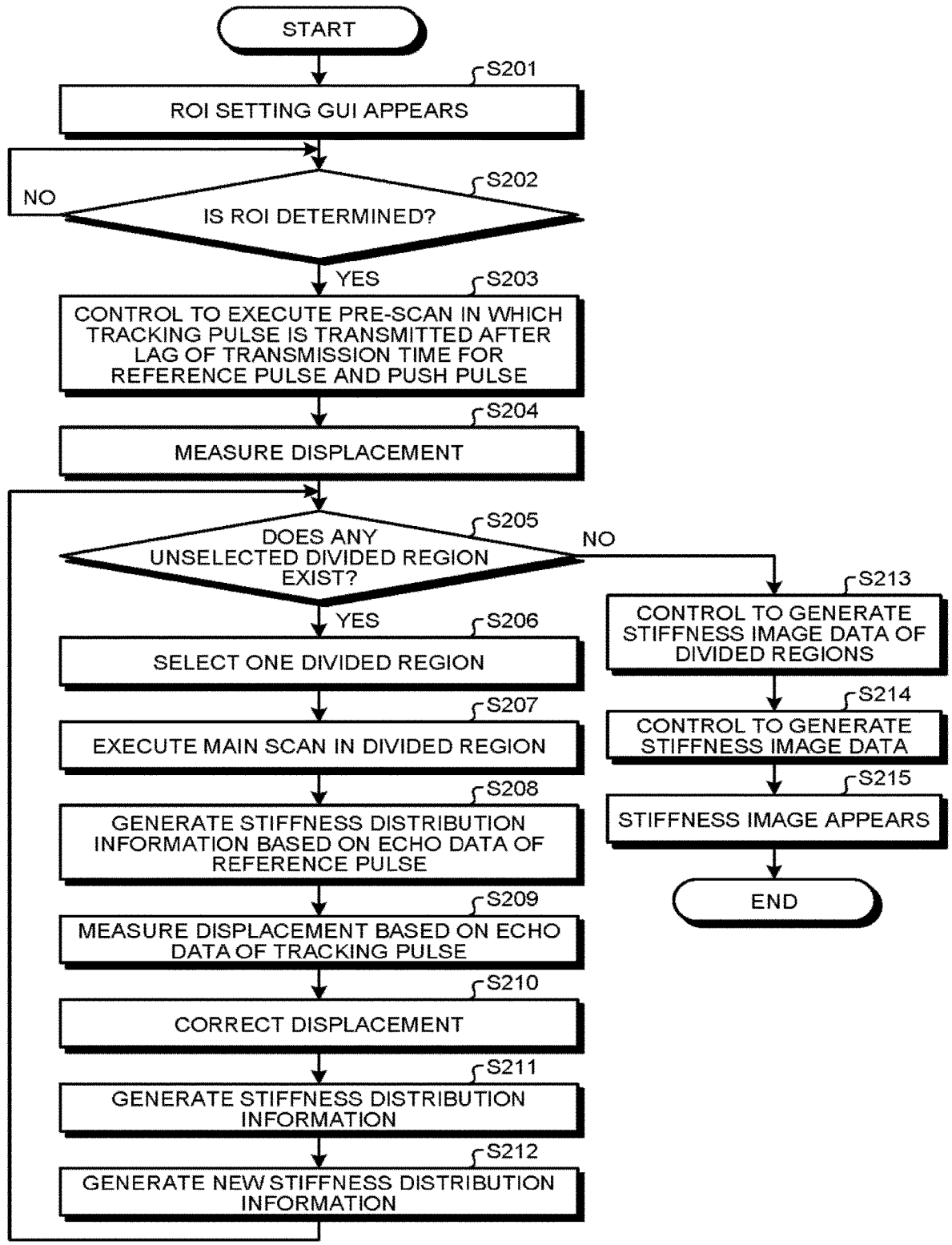
FIG. 10 is a flowchart for explaining an example of the stiffness image generating process according to the second embodiment.

FIG. 10 is a flowchart for explaining an example of the stiffness image generating process according to the second embodiment. This stiffness image generating process is performed when a start instruction to start a stiffness image generation mode for generating a stiffness image is accepted from the operator, in the same manner as in the first embodiment. As illustrated in FIG. 10, the first scan controller 174 allows an ROI setting GUI to appear on the monitor 2, in the same manner as in step 2101 in the first embodiment (step S201).

The first scan controller 174 then determines whether the ROI is determined, in the same manner as in step S102 in the first embodiment (step S202). If the ROI is not determined (No at step 202), the first scan controller 174 performs the determination at step 3202 again.

On the other hand, if the ROI is determined (Yes at step 3202), the first scan controller 174 divides the determined ROT into a plurality of divided regions, calculates the transmission position of push pulses corresponding to each divided region, and controls the transmitter 11 and the receiver 12 so as to execute a pre-scan, for each block 31, for generating echo data of a divided region by transmitting tracking pulses at the timing when the transmission time for reference pulses and push pulses has passed since the start timing of the block 31, in a certain heartbeat (the first heartbeat) indicated by the electrocardiographic waveform (step S203).

The measuring unit 175 then measures the displacement of biological tissue of the subject P, for each divided region, based on the echo data obtained through the pre-scan, in the first heartbeat (step S204).

The second scan controller 176 then determines whether any unselected divided region (an unselected divided region at step S206 described later) exists among a plurality of divided regions (step S205).

If any unselected divided region exists (Yes at step S205), the second scan controller 176 selects one unselected divided region (step S206). The second scan controller 176 then executes a main scan in the divided region selected at step S206, in the second heartbeat (step S207).

The measuring unit 175 then generates stiffness distribution information for the divided region selected at step S206, based on the echo data of reference pulses obtained in the main scan in the second heartbeat (step S208). The measuring unit 175 also measures the displacement of biological tissue of the divided region selected at step S206, based on the echo data of tracking pulses obtained in the main scan in the second heartbeat (step S209).

The corrector 177 then corrects the displacement of biological tissue in the divided region to the displacement of biological tissue caused by a push pulse alone (step S210). The measuring unit 175 then generates stiffness distribution information of the divided region selected at step 3206, based on the corrected displacement (step S211).

The measuring unit 175 then subtracts the stiffness distribution information generated at step 3206 from the stiffness distribution information generated at step S211 to generate new stiffness distribution information (step S212). The process then returns to step S205.

On the other hand, if no unselected divided region exists (No at step S205), the second scan controller 176 controls the image generator 14 so as to generate respective stiffness image data of the divided regions, based on respective stiffness distribution information of the divided regions (stiffness distribution information generated at step S212) (step S213).

The second scan controller 176 then controls the image generator 14 so as to synthesize respective stiffness image data of the divided regions to generate stiffness image data representing a single stiffness image of the ROT (step S214). The second scan controller 176 then allows the stiffness image represented by the generated stiffness image data to appear on the monitor 2 (step S215). The stiffness image generating process then ends. At step 3215, the second scan controller 176 may allow the measured values (for example, stiffness, shear wave speed, displacement) in the ROI of biological tissue of the subject P to appear on the monitor 2.

The ultrasonic diagnostic apparatus according to the second embodiment has been described above. The ultrasonic diagnostic apparatus according to the second embodiment can accurately measure the physical quantity related to stiffness as described above.

Modification to Second Embodiment

In the foregoing second embodiment, the second scan controller 176 may execute a main scan again in the divided region in which the displacement or velocity measured by the measuring unit 175 in a main scan falls outside a predetermined range. Such an embodiment will be described as a modification to the second embodiment.

For example, when the displacement, of biological tissue measured by the measuring unit 175 falls outside a predetermined range in one or more divided regions among a plurality of divided regions in the second heartbeat, the second scan controller 176 invalidates the main scan in all of the divided regions in the second heartbeat and executes a main scan again in all the divided regions in the third heartbeat. The predetermined range is, for example, a range equal to or greater than $(\alpha-\beta)$ and equal to or smaller than $(\alpha+\beta)$ where $\alpha$ is the displacement in the same time phase measured by the measuring unit 175 the pre-scan and $\beta$ is a predetermined value. Alternatively, the predetermined range is a range in which the slope of the graph indicating displacement is almost zero. The same processing as in the second heartbeat is performed in the third and subsequent heartbeats.

This processing invalidates the physical quantity related to stiffness of biological tissue in a divided region obtained through a main scan when there is such a large change in displacement of the pulsation of the heart of the subject P that the physical quantity measured falls outside a predetermined range. A stiffness image thus can be generated without using inaccurate physical quantity related to stiffness. That is, poor accuracy of a stiffness image can be eliminated or minimized.

When, a case that the displacement of biological tissue measured by the measuring unit 175 falls outside a predetermined range in one or more divided regions among a plurality of divided regions occurs in succession in a predetermined number of heartbeats (for example, four heartbeats), the second scan controller 176 allows a message to appear on the monitor 2 to indicate that the measured displacement of biological tissue in the divided region falls outside a predetermined range in a predetermined number of heartbeats in succession. In such a case, the second scan controller 176 may control the transmitter 11 and the receiver 12 such that the preliminary imaging described above is automatically executed again.

The ultrasonic diagnostic apparatus and the control method according to at least one of the foregoing embodiments can accurately obtain the physical quantity related to stiffness.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
   calculation circuitry configured to calculate a first indicator related to motion of biological tissue in a subject, based on echo data obtained through a pre-scan for the subject;
   acquisition circuitry configured to acquire a periodic biological signal of the subject during the pre-scan and after the pre-scan;
   determination circuitry configured to specify one time phase in one cycle of the biological signal acquired during the pre-scan, based on the first indicator, and determine a timing of a main scan for the subject, based on the specified time phase and the biological signal acquired after the pre-scan; and
   scan control circuitry configured to execute the main scan at the timing determined by the determination circuitry, wherein
   the pre-scan is a scan corresponding to one cycle of the biological signal,
   the determination circuitry calculates, during a single cycle of the biological signal of the pre-scan, a time phase difference between the specified time phase and a time phase in which the biological signal acquired during the pre-scan exhibits a distinctive change, and determines, as the timing of the main scan, a timing when the calculated time phase difference has passed since a time phase in which the biological signal acquired after the pre-scan exhibits a change that is substantially identical to the distinctive change, and
   the scan control circuitry executes the main scan in a cycle of the biological signal, the cycle being different from a cycle in which the pre-scan is executed.

2. The ultrasonic diagnostic apparatus according to claim 1, wherein the main scan comprises transmission of a push pulse and transmission and reception of a tracking pulse.

3. The ultrasonic diagnostic apparatus according to claim 1, wherein the pre-scan is a scan executed multiple times in succession.

4. The ultrasonic diagnostic apparatus according to claim 1, wherein the main scan is a scan executed multiple times in succession.

5. The ultrasonic diagnostic apparatus according to claim 1, wherein the determination circuitry specifies a time phase in which an amount of change of the first indicator in a predetermined period falls within a predetermined threshold, and determines a timing of the main scan, based on the specified time phase and the biological signal acquired after the pre-scan.

6. The ultrasonic diagnostic apparatus according to claim 1, wherein
   the determination circuitry determines a timing of the main scan for each of a plurality of regions obtained by dividing a region of interest of the subject, based on the specified time phase and the biological signal acquired after the pre-scan, and
   the scan control circuitry executes the main scan for each of the regions at a timing determined by the determination circuitry.

7. The ultrasonic diagnostic apparatus according to claim 6, wherein
   the calculation circuitry further calculates a second indicator related to motion of the biological tissue in the subject, based on echo data obtained through the main scan for the subject, for the main scan executed in each of the regions, and the scan control circuitry executes the main scan again in a region in which the second indicator calculated in the main scan falls outside a predetermined range.

8. The ultrasonic diagnostic apparatus according to claim 7, wherein when the second indicator falls outside the predetermined range a certain number of times in succession, the scan control circuitry performs control to give notice that the second indicator falls outside the predetermined range the certain number of times in succession.

9. A control method comprising:

calculating an indicator related to motion of biological tissue of a subject, based on echo data obtained through a pre-scan for the subject;

specifying one time phase in one cycle of a periodical biological signal of the subject acquired during the pre-scan by an acquisition circuit for acquiring the biological signal during the pre-scan and after the pre-scan, based on the indicator, and determining a timing of a main scan for the subject, based on the specified time phase and the biological signal acquired after the pre-scan; and executing the main scan at the determined timing, wherein the pre-scan is a scan corresponding to one cycle of the biological signal, the determining comprises calculating, during a single cycle of the biological signal of the pre-scan, a time phase difference between the specified time phase and a time phase in which the biological signal acquired during the pre-scan exhibits a distinctive change, and determining, as the timing of the main scan, a timing when the calculated time phase difference has passed since a time phase in which the biological signal acquired after the pre-scan exhibits a change that is substantially identical to the distinctive change, and the executing comprises the main scan in a cycle of the biological signal, the cycle being different from a cycle in which the pre-scan is executed.

10. The control method according to claim 9, wherein the main scan comprises transmission of a push pulse and transmission and reception of a tracking pulse.

11. The control method according to claim 9, wherein the pre-scan is a scan executed multiple times in succession.

12. The control method according to claim 9, wherein the main scan is a scan executed multiple times in succession.

13. The control method according to claim 9, the control method further comprising:

specifying a time phase in which an amount of change of the first indicator in a predetermined period falls within a predetermined threshold, and determining a timing of the main scan, based on the specified time phase and the biological signal acquired after the pre-scan.

14. The control method according to claim 9, the control method further comprising:

determining a timing of the main scan for each of a plurality of regions obtained by dividing a region of interest of the subject, based on the specified time phase and the biological signal acquired after the pre-scan, and executing the main scan for each of the regions at the determined timing.

* * * * *